(12) United States Patent
Sun et al.

(10) Patent No.: US 9,585,845 B2
(45) Date of Patent: Mar. 7, 2017

(54) ORAL PHARMACEUTICAL COMPOSITION COMPRISING OSELTAMIVIR AND METHOD OF PREPARING THE SAME

(71) Applicant: Zhongshuai Pharmaceutical Sci & Tech Incorporated Co., Ltd., Zhengzhou (CN)

(72) Inventors: Weidong Sun, Zhengzhou (CN); Fengxiao Ren, Zhengzhou (CN)

(73) Assignee: Zhongshuai Pharmaceutical Sci & Tech Co., Ltd., Zhengzhou (CN)

( * ) Notice: Subject to any disclaimer, the term of this patent is extended or adjusted under 35 U.S.C. 154(b) by 0 days.

(21) Appl. No.: 14/992,038

(22) Filed: Jan. 11, 2016

(65) Prior Publication Data

US 2016/0120820 A1    May 5, 2016

Related U.S. Application Data

(63) Continuation-in-part of application No. PCT/CN2014/000836, filed on Sep. 10, 2014.

(30) Foreign Application Priority Data

Jul. 11, 2013 (CN) .......................... 2013 1 0290958

(51) Int. Cl.
*A61K 9/00* (2006.01)
*A61K 9/50* (2006.01)
*A61K 9/20* (2006.01)
*A61K 9/48* (2006.01)
*A61K 31/215* (2006.01)

(52) U.S. Cl.
CPC .......... *A61K 9/5078* (2013.01); *A61K 9/0095* (2013.01); *A61K 9/20* (2013.01); *A61K 9/48* (2013.01); *A61K 9/5026* (2013.01); *A61K 31/215* (2013.01)

(58) Field of Classification Search
CPC .................................................. A61K 9/5078
See application file for complete search history.

(56) References Cited

U.S. PATENT DOCUMENTS

2005/0175689 A1* 8/2005 Kurimoto ............ A61K 9/2081
424/464

FOREIGN PATENT DOCUMENTS

WO    WO 2010143207 A1 * 12/2010 ........... A61K 9/0056

OTHER PUBLICATIONS http://www.hopetop.cn/zzy_en/id/38.html, accessed Aug. 20, 2016.*
http://www.technology-x.net/CN18/201210484183.html, accessed Aug. 20, 2016.*

* cited by examiner

*Primary Examiner* — Paul Dickinson
(74) *Attorney, Agent, or Firm* — Matthias Scholl, PC; Matthias Scholl

(57) ABSTRACT

A pharmaceutical composition, including: an active ingredient-loaded pellet core and a coating layer. The active ingredient of the pellet core is oseltamivir or a pharmaceutically acceptable salt thereof. The active ingredient accounts for between 10 and 40 wt. % of the total weight of the pharmaceutical composition. The coating layer includes a polyacrylic acid resin IV and accounts for between 1 and 50 wt. % of the total weight of the pharmaceutical composition. The pharmaceutical composition has a diameter of between 0.10 and 0.50 mm.

3 Claims, No Drawings

ORAL PHARMACEUTICAL COMPOSITION COMPRISING OSELTAMIVIR AND METHOD OF PREPARING THE SAME

CROSS-REFERENCE TO RELATED APPLICATIONS

This application is a continuation-in-part of International Patent Application No. PCT/CN2014/000836 with an international filing date of Sep. 10, 2014, designating the United States, now pending, and further claims priority benefits to Chinese Patent Application No. 201310290958.4 filed Jul. 11, 2013. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to an oral pharmaceutical composition and a method of preparing the same.

Description of the Related Art

Oseltamivir, having the chemical name of (3R,4R,5S)-4-acetamido-5-amino-3(1-ethylpropoxy)-1-cyclohexene-1-carboxylate and the structural formula (I), can act on neuraminidase (NA), to inhibit the replication and spreading of the viruses.

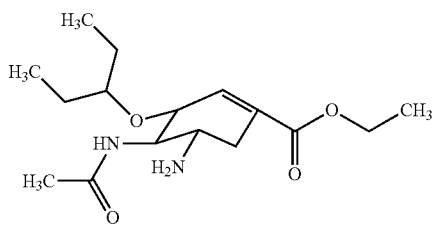

(I)

Because oseltamivir has strong bitter taste and the commercial oseltamivir adopts capsules for the dosage form, it is difficult for children and infants to swallow the oseltamivir capsule. To cover the bitter taste of oseltamivir, various encapsulation techniques have been tried. However, based on conventional encapsulation techniques, the active ingredient cannot be completely covered, or the pill has too large particle size thus affecting the administration, or the pill has too small particle size thus leading to low load efficiency.

SUMMARY OF THE INVENTION

In view of the above-described problems, it is one objective of the invention to provide an oral pharmaceutical composition. The pharmaceutical composition of the invention is odorless and tasteless, and the granularity thereof enables the composition to be prepared into formulations suitable for administration by children and particularly infants, thus being applicable for preventing and treating influenza of children and particularly infants.

It is another objective of the invention to provide a method of preparing the pharmaceutical composition. The components of the pharmaceutical composition is adapted to be processed and coated in a fluidized bed, to yield a stable preparation intermediate, which can be further processed into capsules, orally disintegrating tables, chewable tablets, suspensions, and granules.

To achieve the above objective, in accordance with one embodiment of the invention, there is provided a pharmaceutical composition. The pharmaceutical composition comprises: an active ingredient-loaded pellet core, and a coating layer.

The active ingredient of the pellet core is oseltamivir having the formula I,

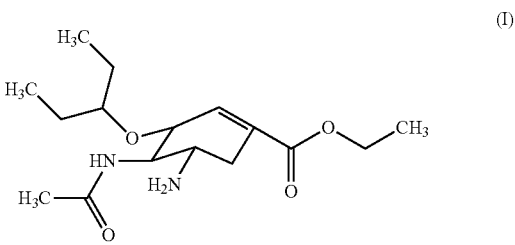 [SMILES: CCOC(=O)C1=CC(OC(CC)CC)C(NC(C)=O)C(N)C1]

(I)

or a pharmaceutically acceptable salt thereof, and accounts for between 10 and 40 wt. % of a total weight of the pharmaceutical composition. The coating layer comprises a polyacrylic acid resin IV and accounts for between 1 and 50 wt. % of the total weight of the pharmaceutical composition. The particle size of the pharmaceutical composition is between 0.10 and 0.50 mm.

In a class of this embodiment, the particle size of the pharmaceutical composition is between 0.15 and 0.35 mm, the coating layer accounts for between 5 and 50 wt. % of the total weight of the pharmaceutical composition, and the salt of oseltamivir is oseltamivir phosphate.

Unless otherwise indicated, oseltamivir in the text refers to oseltamivir phosphate.

In a class of this embodiment, the pellet core is prepared by a blank pellet, the active ingredient, a filler, an adhesive, and an anti-sticking agent. Weight percentages of the components in the pharmaceutical composition are as follows: between 10 and 40 wt. % of the active ingredient, between 20 and 60 wt. % of the blank pellet, between 0 and 50 wt. % of the filler, between 1 and 20 wt. % of the adhesive, and between 0.5 and 5 wt. % of the anti-sticking agent.

In a class of this embodiment, the blank pellet is at least one selected from the group consisting of a sucrose pellet, a microcrystalline cellulose pellet, a starch pellet, a lactose-microcrystalline cellulose pellet, a starch-microcrystalline cellulose pellet, and a sucrose-starch pellet. The filler is at least one selected from the group consisting of sucrose, lactose, mannitol, a starch, a microcrystalline cellulose, an algal polysaccharide, a chitosan. The adhesive is at least one selected from the group consisting of water, ethanol, a hydroxypropyl methyl cellulose, a polyacrylic acid resin, a hydroxypropyl cellulose, a povidone, a polyvinyl alcohol, and a carboxymethylcellulose sodium. The anti-sticking agent is at least one selected from the group consisting of a talc, colloidal silica, magnesium stearate, calcium stearate, magnesium silicate, and glyceryl monostearate.

In a class of this embodiment, the blank pellet is the sucrose pellet; the filler is lactose and/or mannitol; the adhesive is the hydroxypropyl methyl cellulose; and the anti-sticking agent is the talc.

In a class of this embodiment, the weight percentages of the components in the pharmaceutical composition are as follows: between 10 and 30 wt. % of oseltamivir, between 5 and 50 wt. % of the polyacrylic acid resin IV, between 20 and 60 wt. % of the sucrose pellet, between 0 and 50 wt. % of lactose and/or mannitol, between 1 and 20 wt. % of the hydroxypropyl methyl cellulose, and between 0.5 and 50 wt. % of the talc.

In a class of this embodiment, the weight percentages of the components in the pharmaceutical composition are as follows: 23.8 wt. % of oseltamivir, 16.7 wt. % of the polyacrylic acid resin IV, 49.6 wt. % of the sucrose pellet, 7.9 wt. % of the hydroxypropyl methyl cellulose, and 2.0 wt. % of the talc.

In a class of this embodiment, the composition is optionally prepared into capsules, tablets, the pellets, granules, or suspensions.

In accordance with one embodiment of the invention, there is provided a method of preparing the pharmaceutical composition. The method comprises:

1) Grinding a raw material and sieving the ground raw material by a 120-mesh sieve, grinding an excipient and sieving the excipient by a 80-mesh sieve, adding oseltamivir, the filler, and the anti-sticking agent to the adhesive solution while stirring to form a suspension comprising materials for an active ingredient-loaded layer. Preferably, the active ingredient-layering process of the suspension is performed in a fluidized bed or a coating pan. The materials for the active ingredient-loaded layer is atomized at a proper pressure, sprayed into the fluidized bed, so that the materials for the active ingredient-loaded layer are loaded on the blank pellets and form the active ingredient layer thereon at a certain temperature. Under a certain fluidized velocity, the blank pellets are transformed into active ingredient-loaded pellet cores having uniform contents and particle sizes. According to the originally adopted particle size of the blank pellets and the corresponding formulation and technology, the particle size of the active ingredient-loaded pellet cores can be controlled within a range of between 0.10 and 0.50 mm, and preferably within a range of 0.25±0.10 mm.

2) Adding the polyacrylic acid resin IV to an ethanol solution to yield a polyacrylic acid resin IV solution, performing a coating process in the fluidized bed or the coating pan, atomizing the polyacrylic acid resin IV solution at a proper pressure and spraying the polyacrylic acid resin IV solution into the fluidized bed to allow coating materials to adhere to the active ingredient-loaded pellet cores at a certain temperature.

In a class of this embodiment, the adhesive solution is prepared by mixing an adhesive with water, and a weight of the water is between 5 and 100 times a weight of the adhesive. The coating solution is prepared by mixing the polyacrylic acid resin IV with the ethanol solution. The ethanol solution comprises between 50 and 99 wt. % of ethanol. A weight of ethanol is between 5 and 100 times a weight of the polyacrylic acid resin IV.

Advantages of the pharmaceutical composition and the method of preparing the same are further illustrated hereinbelow combining with experiment data.

Test 1 Taste Evaluation

Pellets (comprising 30 mg of oseltamivir) prepared by examples 1-6 and comparative examples 1-3 were collected and tasted.

Results: all pellets prepared by examples 1-6 had no obvious bad taste or acerbity, while the pellets prepared by the comparative examples 1-3 had obvious acerbity.

Test 2 Influence of the Composition of the Invention on Pigeons Vomiting Model

1. Experimental animal: healthy pigeons (both males and females were operable), 350±50 g of weights, common grades, and purchased from a breeding base.

2. Experimental drugs and administration doses:

70 healthy pigeons were randomly divided into 7 groups and adaptively fed with normal diets for 1 week before the experiment. Diets were prohibited within 4 hrs before the experiment, the room temperature was maintained at between 22 and 24° C., and the feeding environment was kept clean and well ventilated. The pigeons were administered with drugs according to the following groups, the administration dosage corresponded to 30 mg oseltamivir per kg of the pigeon's weight, or the equivalent amount of the polyacrylic acid resin IV. The indexes were closely observed, and normal diets were recovered 8 hrs after the drug administration.

Experimental groups 1-3, three groups, administered with composition pellets prepared by Examples 1-3 with a dosage equivalent to 30 mg of oseltamivir per kg of the pigeon's weight.

Contrast group A, one group, administered with the raw material of oseltamivir with a dosage equivalent to 30 mg of oseltamivir per kg of the pigeon's weight.

Contrast group B, one group, administered with the polyacrylic acid resin IV with a dosage equivalent to 30 mg of polyacrylic acid resin IV per kg of the pigeon's weight.

Contrast group C, one group, administered with a physical mixture of polyacrylic acid resin IV and oseltamivir with a ratio of 1:1, and a dosage of the physical mixture was equivalent to 30 mg of oseltamivir per kg of the pigeon's weight.

Contrast group D, one group, administered with the commercial oseltamivir phosphate capsules manufactured by Roche with a dosage equivalent to 30 mg of oseltamivir per kg of the pigeon's weight.

3. Experimental Method

Observation indexes: latent periods of vomiting (the period from the administration to the first vomiting), vomiting times (occurrences of the vomiting after the drug administration, each occurrence of the vomiting refers to the duration from neck stretching, mouth opening, shrugging, and abdominal contraction of the pigeons to recovery of the quiet state of the pigeons), and vomiting frequencies (referring to the times of neck stretching, mouth opening, shrugging, and abdominal contraction of the pigeons).

The pigeons in each group were taken drugs by intragastric administration with a dosage equivalent to 30 mg of oseltamivir per kg of the pigeon's weight. The latent periods of vomiting (min) after the intragastric administration, as well as the vomiting times and the vomiting frequency in 5 hrs after the intragastric administration were recorded.

In each group, the number of the vomiting pigeons (n) was calculated. For the vomiting pigeons (including vomiting with vomitus and dry vomiting in the absence of vomitus), the latent period of vomiting (min, $\bar{x}\pm s$), the average vomit times, and the average vomit frequencies were calculated, and results were listed in Table 1.

TABLE 1

Comparison of vomiting phenomenon among experimental pigeons ($\bar{x} \pm s$, n = 10)

| Groups | Number of vomiting pigeons (n) | Latent period for vomiting (min) | Average vomiting times (within 5 hrs) | Vomiting frequencies (times) | Note |
|---|---|---|---|---|---|
| Example 1 | 2 | 152.3 ± 12.4 | 3.0 | 8.5 ± 0.7 | Dry vomiting |
| Example 2 | 2 | 163.4 ± 16.1 | 2.5 | 9.0 ± 1.4 | Dry vomiting |
| Example 3 | 3 | 156.8 ± 7.9 | 3.4 | 10.0 ± 1.7 | Dry vomiting |
| Contrast group A | 9 | 17.1 ± 6.8 | 10.3 | 15.1 ± 0.9 | Seven times of vomiting with vomitus, and the remaining were dry vomiting |
| Contrast group B | 1 | 132.1 ± 0 | 2.0 | 9.6 ± 0 | Dry vomiting |
| Contrast group C | 8 | 22.3 ± 6.2 | 9.5 | 12.9 ± 2.4 | Six times of vomiting with vomitus, and the remaining were dry vomiting |
| Contrast group D | 7 | 30.3 ± 12.1 | 8.7 | 11.8 ± 1.1 | Six times of vomiting with vomitus, and the remaining were dry vomiting |

It was known from the experiment results that the pigeons administered with the composition of the invention had low occurrence of vomiting, long latent periods of vomiting, and the vomiting times were few and the vomiting frequency was low.

Test 3 Optimized Formula Screening

The optimized formula was screened as follows:

1) Polyacrylic Acid Resin IV

Oseltamivir has strong bitter taste, and when oseltamivir is orally administered and directly contacts with the oral mucosa, the bitter taste can be obviously felt. Thus, to cover the bitter taste and reduce the irritation of oseltamivir, an isolation layer is coated on the active ingredient-loaded pellet cores. The methylcellulose, the polyacrylic acid resin IV, hydroxypropyl methyl cellulose, the hydroxypropyl cellulose, the povidone, the ethyl cellulose were compared, and the polyacrylic acid resin IV was finally selected as the coating material for taste-masking. The polyacrylic acid resin IV is the common coating material for taste-masking, herein different thickness of the polyacrylic acid resin IV layer, i. e., different proportions of the polyacrylic acid resin IV, were adopted to examine the influence thereof on the taste-masking effect.

A large batch of active ingredient-loaded pellet cores were prepared and processed by ethanol solutions comprising the polyacrylic acid resin IV prepared according to the same formula, so as to test the taste-masking effect of different amounts of the ethanol solutions comprising the polyacrylic acid resin IV. It was indicated from the test results that under the same circumstances, the taste-masking effect satisfied the requirements when the proportion of the polyacrylic acid resin IV as the coating layer was 16.7 wt. %. And when the proportion of the polyacrylic acid resin IV was 20 wt. %, the taste-masking effect was slightly better than that of the 16.7 wt. % of the polyacrylic acid resin IV, while in the condition of the 20 wt. % of the polyacrylic acid resin IV, the coating process consumed much time and labor and resulted in energy waste. Thus, the proportion of 16.7 wt. % of the polyacrylic acid resin IV was adopted as the optimized craft formula.

2) Blank Pellets

When adopting the fluidized bed or the coating pan for performing the active ingredient-layering process, the active ingredient contained suspension is required to be adhered to a carrier having a certain particle size. The most common blank carrier in the industrial production is blank small balls, i. e., the blank pellets, prepared using a certain pharmaceutical excipient. According to the difference of the pharmaceutical excipients, the blank pellets can be divided into the sucrose pellets, the microcrystalline cellulose pellets, the starch pellets, the lactose-microcrystalline cellulose pellets, the starch-microcrystalline cellulose pellets, and the sucrose-starch pellets. Of them, the sucrose pellets are the most common blank pellets and feature easy integration, low friability, small granularity deviation, high roundness, and narrow distribution range of the particle size. And it was indicated from the tests that the sucrose pellets satisfied the demands on the blank pellet. Thus, the sucrose pellets were selected as the blank pellets.

3) Adhesive

The addition of a certain amount of adhesive is required to adhere the main drug to the blank pellets. Hydroxypropyl methyl cellulose is white or yellowish powder, odorless, tasteless, stable to light, heat, and moisture, and is water soluble at any pH value at a temperature of less than 60° C. and a mixed solvent (1:1) of ethanol, propanol, or isopropanol having a concentration of 70 wt. % and methylene chloride, thereby being the most widely applied adhesive. Herein the hydroxypropyl methyl cellulose having the low viscosity grade (5 cPa·s) was adopted as the adhesive in the formula for preparing the active ingredient-loaded pellet cores.

Different amounts of the hydroxypropyl methyl cellulose were screened based on the same coating parameters. The recovery rate of the main drug in the active ingredient-loaded pellet cores obtained from the active ingredient-layering process and the influence on the drug dissolution after the active ingredient-layering process was employed as assessment indexes for the screening. It was indicated from the experiment results that under the same circumstance, when the proportion of the hydroxypropyl methyl cellulose as the adhesive was 7.9 wt. %, the recovery rate of the main drug in the active ingredient-loaded pellet cores reached 97.8 wt. %, and such proportion had no influence on the dissolution of the main drug in the pellets.

4) Anti-Sticking Agent

In the active ingredient-layering process and the coating process for preparing the oseltamivir pellets, the active ingredient-loaded pellet cores were easily adhered to each other and aggregated to form clusters. Thus, a certain amount of anti-sticking agent was required, herein the talc which satisfied the standard of the Chinese pharmacopoeia, 2010 edition, was adopted as the anti-sticking agent. The talc is white or off-white, and tiny powder in the absence of grittiness, and has an oily feel when being touched. The talc is odorless, tasteless, and is non-dissolvable in water, diluted acid, and diluted hydroxide alkalis. As the pharmaceutical excipient, the talc features wide range, non-toxicity, odorless, high whiteness, good compatibility, strong glossiness, soft tastes, and strong smooth degree. Besides, the talc has a pH value of between 7 and 9, and the original product characters do not change due to the decomposition thereof.

It was indicated from the experiment results that under the same circumstances, the addition of 2.0 wt. % of the talc was able to obviously improve the phenomenon of mutual adhesion and aggregation of the active ingredient-loaded pellet cores, thus satisfying the requirements.

Advantages of the composition for the oral pharmaceutical pallet and the method of preparing the same of the invention according to embodiments of the invention are summarized as follows:

1. The oseltamivir pellets prepared in the invention has no toxicity or side effects, and thus being convenient for long term treatment of patients and improving the medication compliance. The oseltamivir pellets are odorless and tasteless and have good roundness and no gritty irritation to the oral cavity. The granularity of the oseltamivir pellet can be processed into the administration formulation that is suitable for children particularly infants, so that the oseltamivir pellet can be used in preventing and treating influenza of the children particularly the infants.

2. Both the excipient and the preparation of the oseltamivir pellets of the invention are accessible, feasible, and suitable for large scale of industrial production. The preparation method of the invention has excellent repeatability. Since the pellets of different specification have the same formula and craft, the pellets of different specifications can be obtained as long as changing the filling amount of the pellets. Particularly, the preferred formula and preparation method of the invention are both the best screened technical solutions. The pellets, prepared based on the optimized formula and the active ingredient-layering process in the fluidized bed, are odorless and tasteless and are able to realize the good release performance of the formulation thereof in vivo. Pellets of different specifications can be prepared so as to satisfy the requirements of people with different weights.

3. The oseltamivir pellets of the invention have an effective dose of between 10 and 75 mg and have different specifications corresponding to administration objects of different weights. It is known from the in vivo experiments that when the administration level is between 1.0 and 4.0 mg/kg, the oseltamivir pellets of different specifications have the same in vivo pharmacokinetic parameters, thus satisfying the requirements on the blood concentration in therapy. The oseltamivir pellets of different specifications are all prepared by the same sustained-release pellet. Thus, no changes on the constituents or the proportion of the formula are needed, and the formulas of the oseltamivir pellets of different specifications can be obtained as long as regulating the total amounts of the filled oseltamivir pellets, thereby being much convenient. In the meanwhile, as being prepared by the same type of pellets, the oseltamivir pellets of different specifications have very small difference in the in vitro release and the in vivo pharmacokinetic parameters, F2 are all larger than 90 in different release conditions, thus the medication safety is improved.

4. The physical stability in the granularity, the roundness, and the stability of the oseltamivir pellets of the invention is suitable for the in vivo pharmacokinetic features, thus different oral preparations can be prepared according to different population features and the required doses, such as, tablets, capsules, and dry suspensions. Different formulations and specifications of the oseltamivir pellets are all based on the same in vitro release features and stable preparation process.

5. The oseltamivir pellets have simple and feasible preparation process. The active ingredient-layering process and the centrifugal granulation based on the fluidized bed can be adopted, and the yield thereof reaches 90 wt. %, which satisfies the requirements on the large-scale production. In the laboratory production, between 10000 and 30000 units of magnification production have been accomplished, and the production efficiency is high. In the meanwhile, the release performance of the pellets in vitro under multiple conditions is the same as that of capsules in the market, and the pellets also have bioavailability equivalence as the capsules in the market indicated from the studies on in vivo pharmacokinetics. According to related principle of ICH studies, the pellets can be put into the drug market in the absence of demonstration of the clinical trials.

6. It is indicated from the accelerated stability test that the oseltamivir pellets have stable characters within 12 months, and the active ingredient content and related substances are all within a controllable range, thus the oseltamivir pellets are suitable for industrialized production.

DETAILED DESCRIPTION OF THE EMBODIMENTS

For further illustrating the invention, experiments detailing a pharmaceutical composition and a method of preparing the same are described below. It should be noted that the following examples are intended to describe and not to limit the invention.

Example 1

Pharmaceutical Composition Comprising Oseltamivir Phosphate and Preparation Method Thereof The blank pellets were first conducted with a drug-layering process according to a formula for preparing active ingredient-loaded pellet cores, and the active ingredient-loaded pellet cores were then performed with a coating process for preparing taste-masking pellets, i. e., oseltamivir pellets.

1) Preparation Process of Active Ingredient-Loaded Pellet Cores Comprising Oseltamivir Phosphate Formula for preparing the active ingredient-loaded pellet cores: 150.0 g of sucrose pellets (having particle sizes of between 0.10 and 0.20 mm) as the blank pellet, 82.0 g of oseltamivir phosphate, 28.0 g of a hydroxypropyl methyl cellulose as an adhesive, and 500.0 g of purified water.

Preparation process: 28.0 g of the hydroxypropyl methyl cellulose was added to 500.0 g of the purified water while stirring to dissolve the hydroxypropyl methyl cellulose until a solution was clarified. 82.0 g of oseltamivir phosphate was added to the solution and continued stirring. After 1 hr of stirring, the solution was screened by a 40-mesh sieve to obtain a drug contained solution.

150.0 g of the sucrose pellets (having the particle sizes of between 0.10 and 0.20 mm) were added to a fluidized bed, a temperature in the fluidized bed was regulated to be 50° C., and an air supply rate thereof was controlled at 50 $m^3*h^{-1}$. The prepared drug contained solution was sprayed by a peristaltic pump into an atomization chamber at a flow rate of 2 mL/min in a bottom spray mode for performing the active ingredient-layering process, during which, an atomization pressure was controlled at 1.2 bar, and a solution supply rate was gradually increased to 6 mL/min until the active ingredient contained solution was consumed. After the active ingredient-layering process, resulting pellets were fluidized dried for 30 min in the fluidized bed so as to obtain the active ingredient-loaded pellet cores.

2) Preparation of Taste-Masking Pellets

Formula for the taste-masking pellets: 260.0 g of the active ingredient-loaded pellet cores, 39 g of a polyacrylic acid resin IV, 390 mL of a 95 wt. % ethanol solution.

Preparation process: the polyacrylic acid resin IV having the weight according to the formula was dissolved into the 95 wt. % ethanol solution until the solution was clarified, so that a coating solution was obtained.

260.0 g of the active ingredient-loaded pellet cores were added to the fluidized bed. The temperature in the fluidized bed was regulated to be 35° C., and a dried air flow rate was controlled at 60 $m^3*h^{-1}$. Thereafter, the coating solution was pumped by the peristaltic pump into the atomization chamber at the flow rate of 2 mL/min in the bottom spray mode for performing the coating process, during which, the atomization pressure was controlled at 1.0 bar, and a pumping rate was gradually increased to 10 mL/min until the coating solution was consumed. The temperature in the fluidized bed was increased to 50° C. for fluidized drying resulting pellets for 30 min. After that, pellets having particle sizes of between 0.10 and 0.30 mm were selected and examined to obtain qualified taste-masking pellets.

It should be noted that the purified water and ethanol added in the preparation were finally evaporated from the products in the drying process.

It was known from calculation that weight percentages of each component in the composition pellet comprising oseltamivir phosphate were as follows: 27.4 wt. % of oseltamivir phosphate, 13.0 wt. % of the polyacrylic acid resin IV, 50.2 wt. % of the sucrose pellets, and 9.4 wt. % of the hydroxypropyl methyl cellulose.

Example 2

Pharmaceutical Composition Comprising Oseltamivir and Preparation Method Thereof The blank pellets were first conducted with a drug-layering process according to a formula for preparing active ingredient-loaded pellet cores, and the active ingredient-loaded pellet cores were then performed with a coating process for preparing taste-masking pellets, i. e., oseltamivir pellets.

1) Preparation Process of the Active Ingredient-Loaded Pellet Cores

Formula for preparing the active ingredient-loaded pellet cores: 100.0 g of sucrose pellets (having particle sizes of between 0.15 and 0.25 mm) as the blank pellets, 48.0 g of oseltamivir, 16.0 g of a hydroxypropyl methyl cellulose as an adhesive, 4.0 g of talc as an anti-sticking agent, and 384.0 g of purified water.

Preparation process: 16.0 g of the hydroxypropyl methyl cellulose was added to 384.0 g of the purified water while stirring to dissolve the hydroxypropyl methyl cellulose until a solution was clarified. 48.0 g of oseltamivir and 4.0 g of the talc were added to the solution and continued stirring. After 1 hr of stirring, the solution was screened by a 40-mesh sieve to obtain a drug contained solution.

100.0 g of the sucrose pellets (having the particle sizes of between 0.15 and 0.25 mm) were added to a fluidized bed, a temperature in the fluidized bed was regulated to be 50° C., and an air supply rate thereof was controlled at 50 $m^3*h^{-1}$. The prepared drug contained solution was sprayed by a peristaltic pump into an atomization chamber at a flow rate of 2 mL/min in a bottom spray mode for performing the active ingredient-layering process, during which, an atomization pressure was controlled at 1.0 bar, and a solution supply rate was gradually increased to 5 mL/min until the active ingredient contained solution was consumed. After the active ingredient-layering process, resulting pellets were fluidized dried for 30 min in the fluidized bed so as to obtain the active ingredient-loaded pellet cores.

2) Preparation of Taste-Masking Pellets

Formula for the taste-masking pellets: 168.0 g of the active ingredient-loaded pellet cores, 33.6 g of a polyacrylic acid resin IV, 336 mL of a 95 wt. % ethanol solution.

Preparation process: the polyacrylic acid resin IV having the weight according to the formula was dissolved into the 95 wt. % ethanol solution until the solution was clarified, so that a coating solution was obtained.

168.0 g of the active ingredient-loaded pellet cores were added to the fluidized bed. The temperature in the fluidized bed was regulated to be 35° C., and a dried air flow rate was controlled at 60 $m^3*h^{-1}$. Thereafter, the coating solution was pumped by the peristaltic pump into the atomization chamber at the flow rate of 2 mL/min in the bottom spray mode for performing the coating process, during which, the atomization pressure was controlled at 1.0 bar, and a pumping rate was gradually increased to 8 mL/min until the coating solution was consumed. The temperature in the fluidized bed was increased to 50° C. for fluidized drying resulting pellets for 30 min. After that, pellets having particle sizes of between 0.15 and 0.35 mm were selected and examined to obtain qualified taste-masking pellets.

It should be noted that the purified water and ethanol added in the preparation were finally evaporated from the products in the drying process.

It was known from calculation that weight percentages of each component in the composition pellet comprising oseltamivir were as follows: 23.8 wt. % of oseltamivir, 16.7 wt. % of the polyacrylic acid resin IV, 49.6 wt. % of the sucrose pellets, 7.9 wt. % of the hydroxypropyl methyl cellulose, and 2.0 wt. % of the talc.

Example 3

Pharmaceutical Composition Comprising Oseltamivir Phosphate and Preparation Method Thereof The blank pellets were first conducted with a drug-layering process according to a formula for preparing active ingredient-loaded pellet cores, and the active ingredient-loaded pellet cores were then performed with a coating process for preparing taste-masking pellets, i. e., oseltamivir pellets.

1) Preparation Process of the Active Ingredient-Loaded Pellet Cores

Formula for preparing the active ingredient-loaded pellet cores: 136.0 g of microcrystalline cellulose pellets (having particle sizes of between 0.15 and 0.25 mm) as the blank pallets, 76.2 g of oseltamivir phosphate, 19.3 g of a hydroxypropyl cellulose as an adhesive, 5.0 g of magnesium stearate as an anti-sticking agent, 35.0 g of mannitol as a filler, and 677.5 g of purified water.

Preparation process: 19.3 g of the hydroxypropyl cellulose and 35.0 g of mannitol were added to 677.5 g of the purified water while stirring to dissolve the hydroxypropyl cellulose until a solution was clarified. 76.2 g of oseltamivir phosphate and 5.0 g of magnesium stearate were added to the solution and continued stirring. After 1 hr of stirring, the solution was screened by a 40-mesh sieve to obtain a drug contained solution.

136.0 g of the microcrystalline cellulose pellets (having the particle sizes of between 0.15 and 0.25 mm) were added to a fluidized bed, a temperature in the fluidized bed was regulated to be 45° C., and an air supply rate thereof was controlled at 50 $m^3 * h^{-1}$. The prepared drug contained solution was sprayed by a peristaltic pump into an atomization chamber at a flow rate of 2 mL/min in a bottom spray mode for performing the active ingredient-layering process, during which, an atomization pressure was controlled at 1.4 bar, and a solution supply rate was gradually increased to 8 mL/min until the active ingredient contained solution was consumed. After the active ingredient-layering process, resulting pellets were fluidized dried for 30 min in the fluidized bed so as to obtain the active ingredient-loaded pellet cores.

2) Preparation of Taste-Masking Pellets

Formula for the taste-masking pellets: 271.5 g of the active ingredient-loaded pellet cores, 62.7 g of a polyacrylic acid resin IV, 627 mL of a 97 wt. % ethanol solution.

Preparation process: the polyacrylic acid resin IV having the weight according to the formula was dissolved into the 97 wt. % ethanol solution until the solution was clarified, so that a coating solution was obtained.

271.5 g of the active ingredient-loaded pellet cores were added to the fluidized bed. The temperature in the fluidized bed was regulated to be 35° C., and a dried air flow rate was controlled at 60 $m^3 * h^{-1}$. Thereafter, the coating solution was pumped by the peristaltic pump into the atomization chamber at the flow rate of 2 mL/min in the bottom spray mode for performing the coating process, during which, the atomization pressure was controlled at 1.2 bar, and a pumping rate was gradually increased to 10 mL/min until the coating solution was consumed. The temperature in the fluidized bed was increased to 50° C. for fluidized drying resulting pellets for 30 min. After that, pellets having particle sizes of between 0.15 and 0.35 mm were selected and examined to obtain qualified taste-masking pellets.

It should be noted that the purified water and ethanol added in the preparation were finally evaporated from the products in the drying process.

It was known from calculation that weight percentages of each component in the composition pellet comprising oseltamivir phosphate were as follows: 22.8 wt. % of oseltamivir phosphate, 18.8 wt. % of the polyacrylic acid resin IV, 40.7 wt. % of the microcrystalline cellulose pellets, 10.5 wt. % of the mannitol, 5.8 wt. % of hydroxypropyl cellulose, and 1.5 wt. % of the magnesium stearate.

Example 4

Pharmaceutical Composition Comprising Oseltamivir and Preparation Method Thereof The blank pellets were first conducted with a drug-layering process according to a formula for preparing active ingredient-loaded pellet cores, and the active ingredient-loaded pellet cores were then performed with a coating process for preparing taste-masking pellets, i. e., oseltamivir pellets.

1) Preparation Process of the Active Ingredient-Loaded Pellet Cores

Formula for preparing the active ingredient-loaded pellet cores: 153.0 g of starch pellets (having particle sizes of between 0.10 and 0.15 mm) as the blank pellets, 40.0 g of oseltamivir, 12.0 g of a povidone as an adhesive, 265.0 g of purified water.

Preparation process: 12.0 g of the povidone was added to 265.0 g of the purified water while stirring to dissolve the povidone until a solution was clarified. 40.0 g of oseltamivir was added to the solution and continued stirring. After 1 hr of stirring, the solution was screened by a 40-mesh sieve to obtain a drug contained solution.

100.0 g of the starch pellets (having the particle sizes of between 0.10 and 0.15 mm) were added to a fluidized bed, a temperature in the fluidized bed was regulated to be 45° C., and an air supply rate thereof was controlled at 50 $m^3 * h^{-1}$. The prepared drug contained solution was sprayed by a peristaltic pump into an atomization chamber at a flow rate of 1.5 mL/min in a bottom spray mode for performing the active ingredient-layering process, during which, an atomization pressure was controlled at 1.0 bar, and a solution supply rate was gradually increased to 5 mL/min until the active ingredient contained solution was consumed. After the active ingredient-layering process, resulting pellets were fluidized dried for 30 min in the fluidized bed so as to obtain the active ingredient-loaded pellet cores.

2) Preparation of Taste-Masking Pellets

Formula for the taste-masking pellets: 205.0 g of the active ingredient-loaded pellet cores, 100 g of a polyacrylic acid resin IV, 900 mL of a 97 wt. % acetone solution.

Preparation process: the polyacrylic acid resin IV having the weight according to the formula was dissolved into the 97 wt. % acetone solution until the solution was clarified, so that a coating solution was obtained.

205.0 g of the active ingredient-loaded pellet cores were added to the fluidized bed. The temperature in the fluidized bed was regulated to be 30° C., and a dried air flow rate was controlled at 65 $m^3 * h^{-1}$. Thereafter, the coating solution was pumped by the peristaltic pump into the atomization chamber at the flow rate of 2 mL/min in the bottom spray mode for performing the coating process, during which, the atomization pressure was controlled at 1.2 bar, and a pumping rate was gradually increased to 12 mL/min until the coating solution was consumed. The temperature in the fluidized bed was increased to 50° C. for fluidized drying resulting pellets for 30 min. After that, pellets having particle sizes of between 0.10 and 0.25 mm were selected and examined to obtain qualified taste-masking pellets.

It should be noted that the purified water and acetone added in the preparation were finally evaporated from the products in the drying process.

It was known from calculation that weight percentages of each component in the composition pellet comprising oseltamivir were as follows: 13.1 wt. % of oseltamivir, 32.8 wt.

% of the polyacrylic acid resin IV, 50.2 wt. % of the starch pellets, 3.9 wt. % of the povidone.

Example 5

Pharmaceutical Composition Comprising Oseltamivir Phosphate and Preparation Method Thereof Active ingredient-loaded pellet cores were first prepared according to a formula in a centrifuging coating pan and then performed with a coating process for preparing taste-masking pellets, i. e., oseltamivir pellets.

1) Preparation Process of the Active Ingredient-Loaded Pellet Cores

Formula for preparing the active ingredient-loaded pellet cores: 100.0 g of microcrystalline cellulose as a filler, 80.0 g of oseltamivir phosphate, 16.0 g of a hydroxypropyl cellulose as an adhesive, and 400.0 g of purified water.

Preparation process: 16.0 g of the hydroxypropyl cellulose was added to 400.0 g of the purified water while stirring to dissolve the hydroxypropyl cellulose until a solution was clarified, so that an adhesive solution was obtained.

100.0 g of the microcrystalline cellulose and 80.0 g of oseltamivir phosphate were added to the centrifugal coating pan, a temperature in the centrifugal coating pan was regulated to be 55° C., and an air supply rate thereof was controlled at 70 $m^3*h^{-1}$. The prepared adhesive solution was sprayed into the centrifugal coating pan by a peristaltic pump at a flow rate of 4 mL/min for performing the active ingredient-layering process, during which, an atomization pressure was controlled at 1.5 bar, and a solution supply rate was gradually increased to 8 mL/min until the adhesive solution was consumed. After the active ingredient-layering process, resulting pellets were dried for 30 min in the centrifugal coating pan so as to obtain the active ingredient-loaded pellet cores.

2) Preparation of Taste-Masking Pellets

Formula for the taste-masking pellets: 196.0 g of the active ingredient-loaded pellet cores, 150 g of a polyacrylic acid resin IV, 1350 mL of a 97 wt. % ethanol solution.

Preparation process: the polyacrylic acid resin IV having the weight according to the formula was dissolved into the 97 wt. % ethanol solution until the solution was clarified, so that a coating solution was obtained.

196.0 g of the active ingredient-loaded pellet cores were added to the centrifugal coating pan. The temperature in the centrifugal coating pan was regulated to be 40° C., and a dried air flow rate was controlled at 90 $m^3*h^{-1}$. Thereafter, the coating solution was sprayed by the peristaltic pump into the centrifugal coating pan at the flow rate of 3 mL/min for performing the coating process, during which, the atomization pressure was controlled at 1.2 bar, and the solution supply rate was gradually increased to 10 mL/min until the coating solution was consumed. After the coating process, the temperature in the centrifugal coating pan was increased to 50° C. for fluidized drying resulting pellets for 30 min. After that, pellets having particle sizes of between 0.10 and 0.30 mm were selected and examined to obtain qualified taste-masking pellets.

It should be noted that the purified water and ethanol added in the preparation were finally evaporated from the products in the drying process.

It was known from calculation that weight percentages of each component in the composition pellet comprising oseltamivir phosphate were as follows: 23.1 wt. % of oseltamivir phosphate, 43.4 wt. % of the polyacrylic acid resin IV, 28.9 wt. % of the microcrystalline cellulose, and 4.6 wt. % of hydroxypropyl cellulose.

Example 6

Pharmaceutical Composition Comprising Oseltamivir Phosphate and Preparation Method Thereof Active ingredient-loaded pellet cores were first prepared according to a formula in a centrifuging coating pan and then performed with a coating process for preparing taste-masking pellets, i. e., oseltamivir pellets.

1) Preparation Process of the Active Ingredient-Loaded Pellet Cores

Formula for preparing the active ingredient-loaded pellet cores: 150.0 g of a starch as a filler, 150.0 g of oseltamivir phosphate, 300.0 g of a 75 wt. % ethanol solution.

Preparation process: 150.0 g of the starch and 150.0 g of oseltamivir phosphate were added to the centrifugal coating pan, a temperature in the centrifugal coating pan was regulated to be 45° C., and an air supply rate thereof was controlled at 65 $m^3*h^{-1}$. 300.0 g of the 75 wt. % ethanol solution was sprayed into the centrifugal coating pan by a peristaltic pump at a flow rate of 3 mL/min for performing the active ingredient-layering process, during which, an atomization pressure was controlled at 1.0 bar, and a solution supply rate was gradually increased to 6 mL/min until the adhesive solution was consumed. After the active ingredient-layering process, resulting pellets were dried for 30 min in the centrifugal coating pan so as to obtain the active ingredient-loaded pellet cores.

2) Preparation of Taste-Masking Pellets

Formula for the taste-masking pellets: 240.0 g of the active ingredient-loaded pellet cores, 80 g of a polyacrylic acid resin IV, 720 mL of a 90 wt. % ethanol solution.

Preparation process: the polyacrylic acid resin IV having the weight according to the formula was dissolved into the 90 wt. % ethanol solution until the solution was clarified, so that a coating solution was obtained.

240.0 g of the active ingredient-loaded pellet cores were added to the centrifugal coating pan. The temperature in the centrifugal coating pan was regulated to be 40° C., and a dried air flow rate was controlled at 70 $m^3*h^{-1}$. Thereafter, the coating solution was sprayed by the peristaltic pump into the centrifugal coating pan at the flow rate of 2 mL/min for performing the coating process, during which, the atomization pressure was controlled at 1.4 bar, and the solution supply rate was gradually increased to 6 mL/min until the coating solution was consumed. After the coating process, the temperature in the centrifugal coating pan was increased to 45° C. for fluidized drying resulting pellets for 30 min. After that, pellets having particle sizes of between 0.10 and 0.25 mm were selected and examined to obtain qualified taste-masking pellets.

It should be noted that the purified water and ethanol added in the preparation were finally evaporated from the products in the drying process.

It was known from calculation that weight percentages of each component in the composition pellet comprising oseltamivir phosphate were as follows: 37.5 wt. % of oseltamivir phosphate, 25.0 wt. % of the polyacrylic acid resin IV, and 37.5 wt. % of the starch.

Example 7

Pharmaceutical Composition Comprising Oseltamivir Phosphate and Preparation Method Thereof Active ingredient-loaded pellet cores were first prepared according to a formula by squeezing and rolling process and then performed with a coating process for preparing taste-masking pellets, i. e., oseltamivir pellets.

1) Preparation Process of the Active Ingredient-Loaded Pellet Cores

Formula for preparing the active ingredient-loaded pellet cores: 200.0 g of microcrystalline cellulose as a filler, 194.0 g of oseltamivir phosphate, 6.0 g of a hydroxypropyl methyl cellulose as an adhesive, and 200.0 g of purified water.

Preparation process: 6.0 g of the hydroxypropyl methyl cellulose was added to 200.0 g of the purified water while stirring to dissolve the hydroxypropyl methyl cellulose until a solution was clarified, so that an adhesive solution was obtained.

200.0 g of the microcrystalline cellulose and 194.0 g of oseltamivir phosphate were uniformly mixed, and the adhesive solution was added to prepare granules. A refrigerated machine was opened and a temperature therein was controlled to be between 3 and 15° C. The granules were then transferred in a feed chute and squeezed by a sieve plate having a pore size of 0.25 mm to prepare strips. The strips were then put in a cutting-rolling barrel where the strips were cut and rolled. After the rolling, pellets were transferred to a coven for drying at a temperature of 60° C. for 4 hrs, and those having particle sizes of between 0.10 and 0.30 mm were selected and examined to obtain qualified active ingredient-loaded pellet cores.

2) Preparation of Taste-Masking Pellets

Formula for the taste-masking pellets: 400.0 g of the active ingredient-loaded pellet cores, 100 g of a polyacrylic acid resin IV, 900 mL of a 95 wt. % ethanol solution.

Preparation process: the polyacrylic acid resin IV having the weight according to the formula was dissolved into the 95 wt. % ethanol solution until the solution was clarified, so that a coating solution was obtained.

400.0 g of the active ingredient-loaded pellet cores were added to a fluidized bed. The temperature in the fluidized bed was regulated to be 35° C., and a dried air flow rate was controlled at 65 $m^3*h^{-1}$. Thereafter, the coating solution was sprayed by the peristaltic pump into an atomization chamber at the flow rate of 3 mL/min in a bottom spray mode for performing the coating process, during which, the atomization pressure was controlled at 1.2 bar, and a solution supply rate was gradually increased to 12 mL/min until the coating solution was consumed. After the coating process, the temperature in the centrifugal coating pan was increased to 50° C. for fluidized drying resulting pellets for 30 min. After that, pellets having particle sizes of between 0.10 and 0.30 mm were selected and examined to obtain qualified taste-masking pellets.

It should be noted that the purified water and ethanol added in the preparation were finally evaporated from the products in the drying process.

It was known from calculation that weight percentages of each component in the composition pellet comprising oseltamivir phosphate were as follows: 38.8 wt. % of oseltamivir phosphate, 20.0 wt. % of the polyacrylic acid resin IV, 40.0 wt. % of the microcrystalline cellulose, and 1.2 wt. % of the hydroxypropyl methyl cellulose.

Comparative Example 1

Pellets a Comprising Oseltamivir Phosphate and Preparation Method Thereof

Formula for preparing the pellets A comprising oseltamivir phosphate: 150.0 g of sucrose pellets (having particle sizes of between 0.10 and 0.20 mm) as blank pellets, 82.0 g of oseltamivir phosphate, 28.0 g of a hydroxypropyl methyl cellulose as an adhesive, and 500.0 g of purified water.

Preparation process: 28.0 g of the hydroxypropyl methyl cellulose was added to 500.0 g of the purified water while stirring to dissolve the hydroxypropyl methyl cellulose until a solution was clarified. 82.0 g of oseltamivir phosphate was added to the solution and continued stirring. After 1 hr of stirring, the solution was screened by a 40-mesh sieve to obtain a drug contained solution.

150.0 g of the sucrose pellets (having the particle sizes of between 0.10 and 0.20 mm) were added to a fluidized bed, a temperature in the fluidized bed was regulated to be 50° C., and an air supply rate thereof was controlled at 50 $m^3*h^{-1}$. The prepared drug contained solution was sprayed by a peristaltic pump into an atomization chamber at a flow rate of 2 mL/min in a bottom spray mode for performing the active ingredient-layering process, during which, an atomization pressure was controlled at 1.2 bar, and a solution supply rate was gradually increased to 6 mL/min until the active ingredient contained solution was consumed. After the active ingredient-layering process, resulting pellets were fluidized dried for 30 min in the fluidized bed so as to obtain the pellets A comprising oseltamivir phosphate.

Comparative Example 2

Pellets B Comprising Oseltamivir Phosphate and Preparation Method Thereof

The blank pellets were first conducted with a drug-layering process according to a formula for preparing active ingredient-loaded pellet cores, and the active ingredient-loaded pellet cores were then performed with a coating process for preparing the pellets B comprising oseltamivir phosphate.

1) Preparation Process of Active Ingredient-Loaded Pellet Cores Comprising Oseltamivir Phosphate Formula for preparing the active ingredient-loaded pellet cores: 150.0 g of sucrose pellets (having particle sizes of between 0.10 and 0.20 mm) as the blank pellet, 82.0 g of oseltamivir phosphate, 28.0 g of a hydroxypropyl methyl cellulose as an adhesive, and 500.0 g of purified water.

Preparation process: 28.0 g of the hydroxypropyl methyl cellulose was added to 500.0 g of the purified water while stirring to dissolve the hydroxypropyl methyl cellulose until a solution was clarified. 82.0 g of oseltamivir phosphate was added to the solution and continued stirring. After 1 hr of stirring, the solution was screened by a 40-mesh sieve to obtain a drug contained solution.

150.0 g of the sucrose pellets (having the particle sizes of between 0.10 and 0.20 mm) were added to a fluidized bed, a temperature in the fluidized bed was regulated to be 50° C., and an air supply rate thereof was controlled at 50 $m^3*h^{-1}$. The prepared drug contained solution was sprayed by a peristaltic pump into an atomization chamber at a flow rate of 2 mL/min in a bottom spray mode for performing the active ingredient-layering process, during which, an atomization pressure was controlled at 1.2 bar, and a solution supply rate was gradually increased to 6 mL/min until the active ingredient contained solution was consumed. After the active ingredient-layering process, resulting pellets were fluidized dried for 30 min in the fluidized bed so as to obtain the active ingredient-loaded pellet cores.

2) Preparation of the Pellets B Comprising Oseltamivir Phosphate

Formula for the pellets B comprising oseltamivir phosphate: 260.0 g of the active ingredient-loaded pellet cores, 52 g of the hydroxypropyl methyl cellulose, and 520 g of deionized water.

Preparation process: the hydroxypropyl methyl cellulose having the weight according to the formula was collected, the deionized water was added to dissolve the hydroxypropyl methyl cellulose until a solution was clarified so that a coating solution was obtained.

260.0 g of the active ingredient-loaded pellet cores were added to the fluidized bed. The temperature in the fluidized bed was regulated to be 50° C., and a dried air flow rate was controlled at 60 $m^3*h^{-1}$. Thereafter, the coating solution was pumped by the peristaltic pump into the atomization chamber at the flow rate of 2 mL/min in the bottom spray mode for performing the coating process, during which, the atomization pressure was controlled at 1.4 bar, and a pumping rate was gradually increased to 8 mL/min until the coating solution was consumed. The temperature in the fluidized bed was increased to 60° C. for fluidized drying resulting pellets for 30 min. After that, pellets having particle sizes of between 0.10 and 0.30 mm were selected and examined to obtain the qualified pellets B comprising oseltamivir phosphate.

Comparative Example 3

Pellets C Comprising Oseltamivir Phosphate and Preparation Method Thereof

Active ingredient-loaded pellet cores were first prepared according to a formula, and then the active ingredient-loaded pellet cores were prepared into the pellets C comprising oseltamivir phosphate.

1) Preparation Process of the Active Ingredient-Loaded Pellet Cores

Formula for preparing the active ingredient-loaded pellet cores: 100.0 g of microcrystalline cellulose as a filler, 80.0 g of oseltamivir phosphate, 16.0 g of a hydroxypropyl cellulose as an adhesive, and 400.0 g of purified water.

Preparation process: 16.0 g of the hydroxypropyl cellulose was added to 400.0 g of the purified water while stirring to dissolve the hydroxypropyl cellulose until a solution was clarified, so that an adhesive solution was obtained.

100.0 g of the microcrystalline cellulose and 80.0 g of oseltamivir phosphate were added to a centrifugal coating pan, a temperature in the centrifugal coating pan was regulated to be 55° C., and an air supply rate thereof was controlled at 70 $m^3*h^{-1}$. The prepared adhesive solution was sprayed into the centrifugal coating pan by a peristaltic pump at a flow rate of 4 mL/min for performing the active ingredient-layering process, during which, an atomization pressure was controlled at 1.5 bar, and a solution supply rate was gradually increased to 8 mL/min until the adhesive solution was consumed. After the active ingredient-layering process, resulting pellets were dried for 30 min in the centrifugal coating pan so as to obtain the active ingredient-loaded pellet cores.

2) Preparation Process of the Pellets C Comprising Oseltamivir Phosphate

Formula for preparing the pellets C comprising oseltamivir phosphate: 196.0 g of the active ingredient-loaded pellet cores, 100 g of Opadry, and 1000 g of deionized water.

Preparation process: Opadry having the weight according to the formula was added to the deionized water and stirred for 1 hr, a resulting solution was screened by a 40-mesh sieve to obtain a coating solution.

196.0 g of the active ingredient-loaded pellet cores were added to the centrifugal coating pan. The temperature in the centrifugal coating pan was regulated to be 45° C., and a dried air flow rate was controlled at 90 $m^3*h^{-1}$. Thereafter, the coating solution was sprayed by the peristaltic pump into the centrifugal coating pan at the flow rate of 3 mL/min for performing the coating process, during which, the atomization pressure was controlled at 1.4 bar, and the solution supply rate was gradually increased to 12 mL/min until the coating solution was consumed. After the coating process, the temperature in the centrifugal coating pan was increased to 50° C. for fluidized drying resulting pellets for 30 min. After that, pellets having particle sizes of between 0.10 and 0.30 mm were selected and examined to obtain the qualified pellets C comprising oseltamivir phosphate.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method of preparing a pharmaceutical composition, the method comprising:
   1) grinding and sieving an active ingredient through a 120-mesh sieve to yield a ground active ingredient;
   2) grinding and sieving a filler through an 80-mesh sieve to yield a ground filler;
   3) grinding and sieving an anti-sticking agent through an 80-mesh sieve to yield a ground anti-sticking agent;
   4) dissolving an adhesive in water to form an adhesive solution;
   5) mixing the ground active ingredient, the ground filler, and the ground anti-sticking agent to yield a mixture, then adding the mixture to the adhesive solution and stirring to form an active ingredient-containing suspension, performing a drug-layering process in a fluidized bed or a coating pan to load the active ingredient-containing suspension on a blank pellet to form an active ingredient-loaded pellet core; and
   6) dissolving a coating material in an ethanol solution to obtain a coating solution, and coating the coating solution on the active ingredient-loaded pellet core in the fluidized bed or the coating pan to form the pharmaceutical composition;

wherein:
   the active ingredient is oseltamivir or a pharmaceutically-acceptable salt thereof.

2. The method of claim 1, wherein
   a weight of the water in the adhesive solution is between 5 and 100 times a weight of the adhesive;
   the ethanol solution comprises between 50 and 99 wt. % of ethanol; and
   a weight of the ethanol is between 5 and 100 times a weight of the coating material.

3. The method of claim 1, wherein:
the pharmaceutical composition comprises the active ingredient-loaded pellet core and the coating material;
the coating material accounts for between 5 and 50 wt. % of a total weight of the pharmaceutical composition;
the active ingredient-loaded pellet core comprises the following components in the following weight percentage: the active ingredient 10-40%, the blank pellet 20-60%, the filler 0-50%, the adhesive 1-20%, and the anti-sticking agent 0.5-5%.

* * * * *